United States Patent [19]

Ramel

[11] Patent Number: 5,540,709
[45] Date of Patent: Jul. 30, 1996

[54] LANCET DEVICE

[75] Inventor: Urs A. Ramel, Sunnyvale, Calif.

[73] Assignee: Actimed Laboratories, Inc., Burlington, N.J.

[21] Appl. No.: 342,417

[22] Filed: Nov. 16, 1994

Related U.S. Application Data

[62] Division of Ser. No. 121,035, Sep. 13, 1993, Pat. No. 5,366,470, which is a continuation of Ser. No. 690,376, Nov. 12, 1991, abandoned.

[51] Int. Cl.⁶ ........................................ A61B 17/32
[52] U.S. Cl. ........................... 606/183; 606/182; 604/157
[58] Field of Search ................................ 606/182, 183, 606/185, 186; 604/137, 157; 128/770

[56] References Cited

U.S. PATENT DOCUMENTS

| | | | |
|---|---|---|---|
| Re. 32,922 | 5/1989 | Levin et al. | 128/314 |
| 1,921,034 | 8/1933 | Marche | 128/218 |
| 2,699,784 | 1/1955 | Krayl | 128/333 |
| 2,704,072 | 3/1955 | Sarnoff | 128/218 |
| 2,804,074 | 8/1957 | Hill | 128/218 |
| 2,832,339 | 4/1958 | Sarnoff et al. | 128/218 |
| 3,030,959 | 4/1962 | Grünert | 128/329 |
| 3,208,452 | 9/1965 | Stern | 606/182 |
| 3,543,603 | 12/1970 | Gley | 74/527 |
| 3,584,626 | 6/1971 | Johansson | 128/218 |
| 3,612,051 | 10/1971 | Arce | 128/215 |
| 3,643,649 | 2/1972 | Amato | 128/1 R |
| 3,892,237 | 7/1975 | Steiner | 128/216 |
| 4,139,011 | 2/1979 | Benoit et al. | 128/329 R |
| 4,164,224 | 8/1979 | Hastings | 128/330 |
| 4,203,446 | 5/1980 | Höfert et al. | 128/329 |
| 4,226,235 | 10/1980 | Sarnoff et al. | 128/128 F |
| 4,316,463 | 2/1982 | Schmitz et al. | 128/218 F |
| 4,329,988 | 5/1982 | Sarnoff et al. | 128/218 F |
| 4,375,815 | 3/1983 | Burns | 128/314 |
| 4,378,015 | 3/1983 | Wardlaw | 128/218 F |
| 4,388,925 | 6/1983 | Burns | 128/314 |
| 4,416,279 | 11/1983 | Linder et al. | 606/182 |
| 4,449,529 | 5/1984 | Burns et al. | 128/314 |
| 4,452,243 | 6/1984 | Leopoldi et al. | 128/314 |
| 4,469,110 | 9/1984 | Slama | 128/770 |
| 4,484,910 | 11/1984 | Sarnoff et al. | 604/136 |
| 4,503,856 | 3/1985 | Cornell et al. | 128/314 |
| 4,512,767 | 4/1985 | Denance | 604/137 |
| 4,517,978 | 5/1985 | Levin et al. | 128/314 |
| 4,577,630 | 3/1986 | Nitzsche et al. | 128/314 |
| 4,580,565 | 4/1986 | Cornell et al. | 128/314 |
| 4,616,649 | 10/1986 | Burns | 128/314 |
| 4,637,403 | 1/1987 | Garcia et al. | 128/770 |
| 4,653,513 | 3/1987 | Dombrowski | 128/765 |
| 4,665,912 | 5/1987 | Burton | 128/303 |
| 4,723,937 | 2/1988 | Sarnoff et al. | 604/90 |
| 4,747,414 | 5/1988 | Brossel | 128/754 |
| 4,817,603 | 4/1989 | Turner et al. | 606/182 |
| 4,850,973 | 7/1989 | Jordan et al. | 604/157 |
| 4,858,607 | 8/1989 | Jordan et al. | 128/324 |
| 4,869,249 | 9/1989 | Crossman et al. | 128/314 |
| 4,892,097 | 1/1990 | Ramalletta et al. | 606/182 |
| 4,895,147 | 1/1990 | Bodicky et al. | 606/182 |
| 4,902,279 | 2/1990 | Schmidtz et al. | 604/134 |

(List continued on next page.)

FOREIGN PATENT DOCUMENTS 2316909  2/1977  France .

*Primary Examiner*—Michael H. Thaler
*Attorney, Agent, or Firm*—Dechert Price & Rhoads

[57] ABSTRACT

A lancet device includes a body within which is slidably located a trigger and fixedly located a base. The base contains, in an armed position, the lance with its needle and a spring affixed to the lance. The trigger includes a mechanism to release the lance during use.

In a preferred embodiment, the lancet device of the present invention is self-activated by the finger (or other body part) to be pierced. Depression of the trigger with the finger releases the lance and the spring so that the needle protrudes through an orifice in the end of the trigger and pierces the tissue. Because the spring is held in a pre-armed position, release of the spring is consistent, and reproducibility of incision is well controlled.

5 Claims, 11 Drawing Sheets

U.S. PATENT DOCUMENTS

| | | | |
|---|---|---|---|
| 4,924,879 | 5/1990 | O'Brien | 128/770 |
| 4,976,724 | 12/1990 | Nieto et al. | 606/182 |
| 5,026,349 | 6/1991 | Schmitz et al. | 604/134 |
| 5,026,388 | 6/1991 | Ingalz | 606/182 |
| 5,100,427 | 3/1992 | Crossman et al. | 606/182 |
| 5,104,380 | 4/1992 | Holman et al. | 604/117 |
| 5,114,404 | 5/1992 | Paxton et al. | 604/110 |
| 5,133,730 | 7/1992 | Biro et al. | 606/182 |
| 5,141,496 | 8/1992 | Dalto et al. | 604/117 |
| 5,152,775 | 10/1992 | Ruppert | 606/182 |
| 5,196,025 | 3/1993 | Ranalletta et al. | 606/182 |
| 5,209,755 | 5/1993 | Abrahan et al. | 606/132 |
| 5,211,652 | 5/1993 | Derbyshire | 606/182 |
| 5,267,963 | 12/1993 | Bachynsky | 606/134 |
| 5,269,799 | 12/1993 | Daniel | 606/182 |
| 5,273,519 | 12/1993 | Koros et al. | 606/83 |
| 5,282,822 | 2/1994 | Macors et al. | 606/182 |
| 5,300,030 | 4/1994 | Crossman et al. | 604/136 |
| 5,314,442 | 5/1994 | Morita | 606/182 |
| 5,318,584 | 6/1994 | Lange et al. | 606/182 |
| 5,320,609 | 6/1994 | Haber et al. | 604/135 |
| 5,324,303 | 6/1994 | Strong et al. | 606/181 |

5,540,709

LANCET DEVICE

This is a division of application Ser. No. 08/121,035 filed Sep. 13, 1993, now U.S. Pat. No. 5,366,470, which is a continuation of application Ser. No. 07/690,376 filed on Nov. 12, 1991, now abandoned.

BACKGROUND OF THE INVENTION

This invention relates to a lancet device for use in taking capillary blood samples by pricking a body tissue, such as a fingertip.

In the case of certain diseases, such as diabetes, or test kits, such as cholesterol test kits, a patient is required to provide small specimens of blood for analysis. This involves pricking a finger or other suitable body part in order to obtain the blood specimen. It is physiologically and psychologically difficult for many people to prick their own finger with a hand-held needle, which must be sterile.

Other lancet devices for obtaining blood samples, such as are disclosed in U.S. Pat. Nos. 4,869,249 and 4,817,603, include a cap which is used to protect the needle or to keep the needle sterile. This makes manufacturing of these devices more difficult and costly, and makes the device harder to use.

In other devices, a spring used to shoot a needle into the tissue is compressed during use by the trigger mechanism, which can lead to misfiring or skewing of the spring so that the incision made is not suitable for obtaining a blood sample. Also, two hands are required for operation of many of these devices.

Thus, there is a need for a simple, inexpensive, reliable, self-activating, disposable lancet device in which reproducibility of suitable incisions is well controlled.

SUMMARY OF THE INVENTION

It is an object of the present invention to provide an improved lancet device.

In one embodiment, the present invention provides a lancet device comprising a body within which is slidably located a trigger and fixedly located a base. The base contains, in an armed position, a lance with its needle and a spring affixed to the lance. The trigger includes means to release the lance during use.

In a preferred embodiment, the lancet device of the present invention is self-activated by the finger (or other body part) to be pierced. Depression of the trigger with the finger releases the lance and the spring so that the needle protrudes through an orifice in one end of the trigger and pierces the tissue of the finger. Because the spring is held in a pre-armed position, release of the spring is consistent, and reproducibility of incision is well controlled.

Other objects, features and advantages of the present invention will become apparent from the following detailed description when taken in conjunction with the accompanying drawings.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 1:
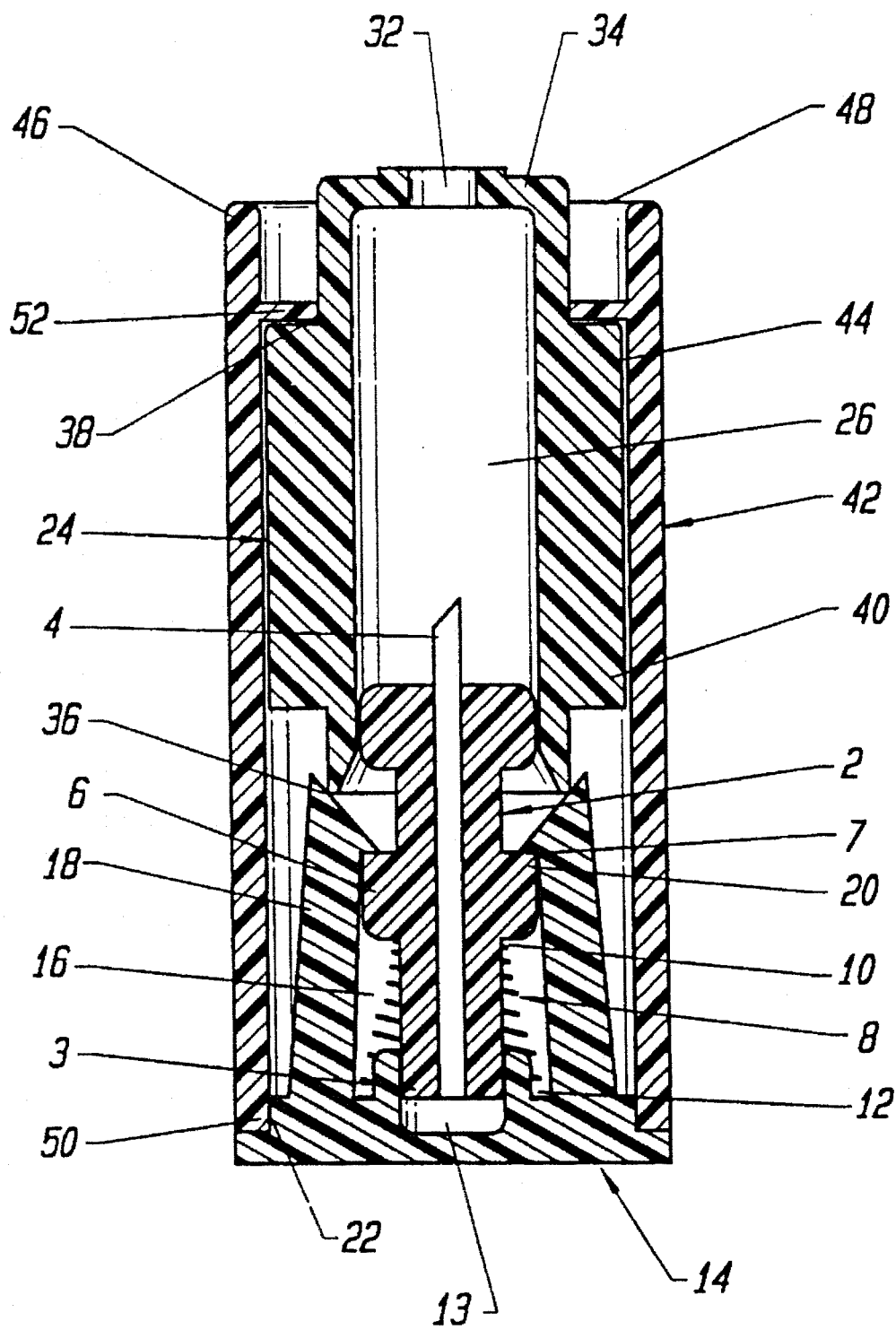
FIG. 1 shows one embodiment in a longitudinal cross-section through the assembled lancet device.
Figure 6:
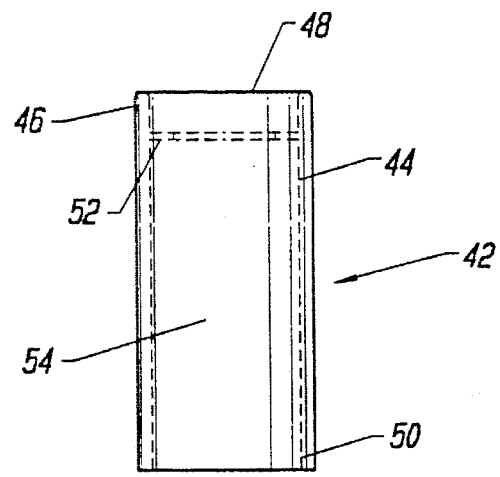
FIG. 6 is a side view of the body of the embodiment shown in FIG. 1.
Figure 5:
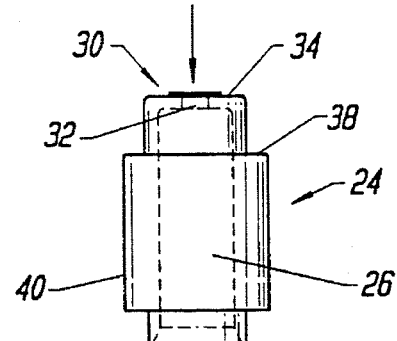
FIG. 5 is a side view of the trigger of the embodiment shown in FIG. 1.
Figure 2:
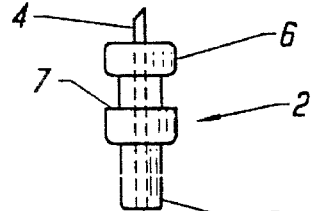
FIG. 2 is a side view of the lance of the embodiment shown in FIG. 1.
Figure 3:
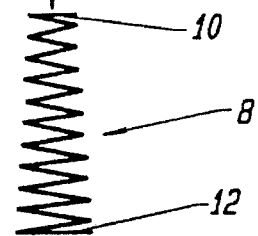
FIG. 3 is a side view of the spring of the embodiment shown in FIG. 1.
Figure 4:
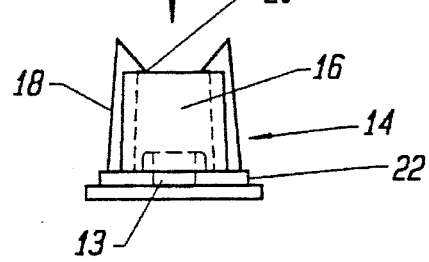
FIG. 4 is a side view of the base of the embodiment shown in FIG. 1.

One embodiment of the disposable lancet device 100 shown assembled in FIG. 1 and in an exploded view in FIGS. 2–6 comprises a body 42 with a lip 46 extending from an aligning ring 52. The trigger 24 is slidably located in barrel 54 of body 42. Its end 30 containing an orifice 32 is aligned so that end 30 is in about the same plane 48 as the edge of lip 46 which is at the open end of body 42.

In a preferred embodiment, end 30 of trigger 24 is aligned in plane 48 by means of aligning edge 38 on trigger 24 and aligning ring 52 on inner surface 44 of body 42.

Means are provided for guiding and centering trigger 24 in barrel 54 of body 42. In a preferred embodiment, guiding ring 40 of trigger 24 serves this function.

The base 14 is fixedly attached to body 42. In a preferred embodiment, this is provided by means of snap fit edge 22 which is in contact with snap fit edge 50 of base 42. Other means of attachment, such as sonic welding, are also possible.

End 12 of spring 8 is fixedly attached to button 13 of base 14. End 10 of spring 8 is fixedly attached to shaft 6 of lance 2. Spring 8, shaft 6 and needle 4 thus provide a lance means. In a preferred embodiment, end 12 is greater in diameter than end 10 to form a tapered spring configuration. Using this tapered spring configuration allows the coils of spring 8 to compress within one another without twisting when they are compressed in an armed position. When a uniform diameter spring is compressed, it may twist or skew. Thus, using a tapered spring helps ensure reproducible release without skewing of the spring. This provides reproducible, centered, piercing force to the lance. In one preferred embodiment, end 12 is about 250 mils in diameter and end 10 is about 150 mils in diameter.

Base 14 comprises retaining means to keep lance 2 and spring 8 in a pre-armed position in well 16. In a preferred embodiment, shaft 6 of lance 2 has an edge 7 which will be caught by clip 20 of arm 18 of base 14 when the lancet device 100 is in the armed position. Spring 8 is compressed, edge 7 is caught by clips 20 of base 14 so that base 14 retains lance 2 and spring 8 in an armed position in well 16. The lance means is thus located in base 14 during manufacture, shipping and storage of the device prior to use.

Figure 7:
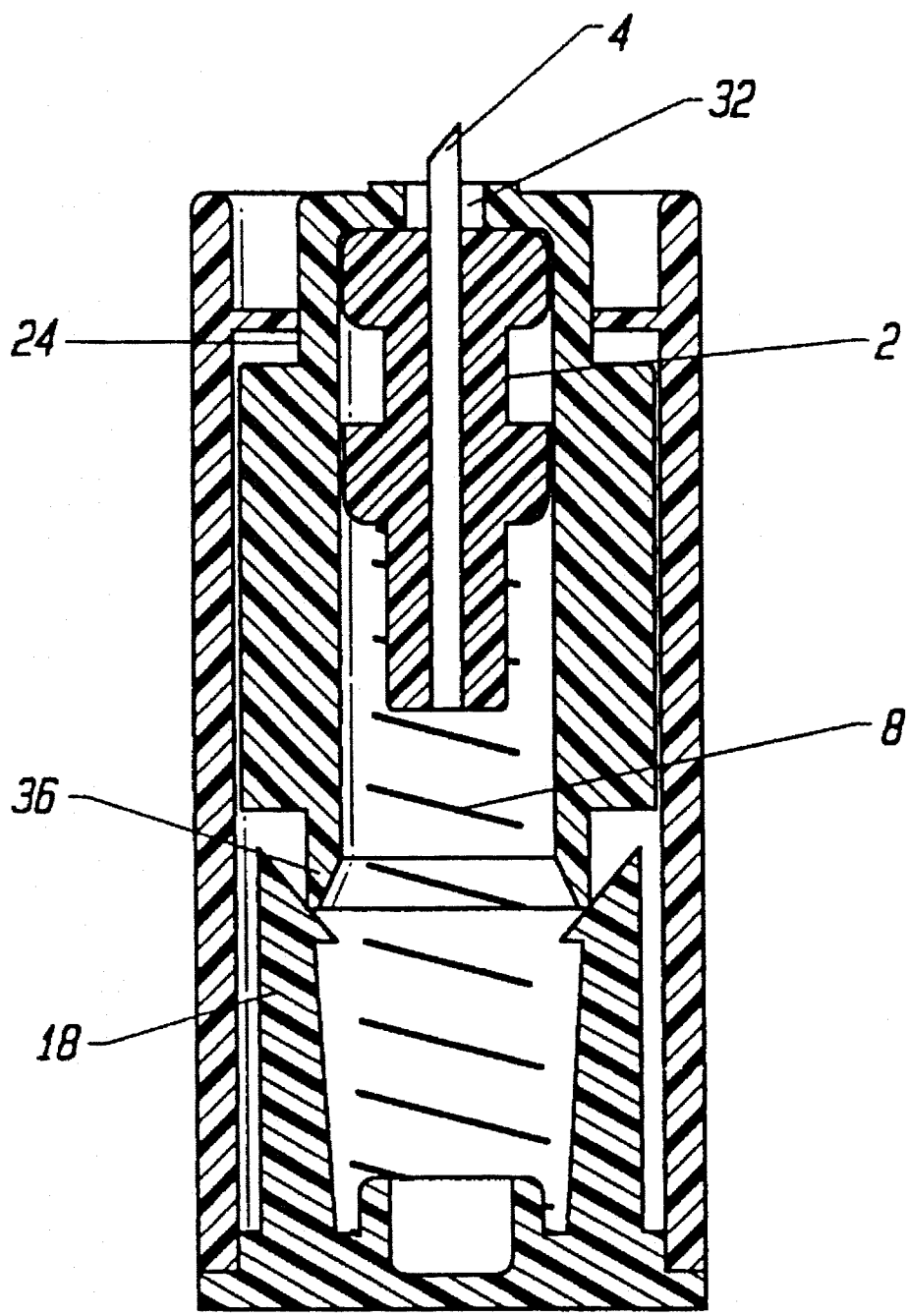
FIG. 7 shows the lancet device of the embodiment shown in FIG. 1 in firing position.

To use lancet device 100, a body part, such as a finger, to be pierced is placed over orifice 32 and trigger 24 is then depressed. This causes clip-deflecting edges 36 to spread arms 18 and release lance 2 and spring 8. Needle 4 is centered and guided through the hollow center 26 of trigger 24 by shaft 6. The force of decompression of spring 8 pushes needle 4 through orifice 32 to pierce the finger depressing trigger 24. This can be seen in FIG. 7. The depth of penetration of needle 4 is controlled by the length of the needle and the thickness of end wall 34. Because the body part to be pierced is the body part which depresses trigger 24, this lancet device is self-activating. This feature makes the lancet device of the present invention simple to use, as it may be operated with one hand. In one preferred embodiment, end wall 34 is 20 to 60 mils thick and the protruding end of needle 4 is 1 to 2.5 mm long.

Figure 9:
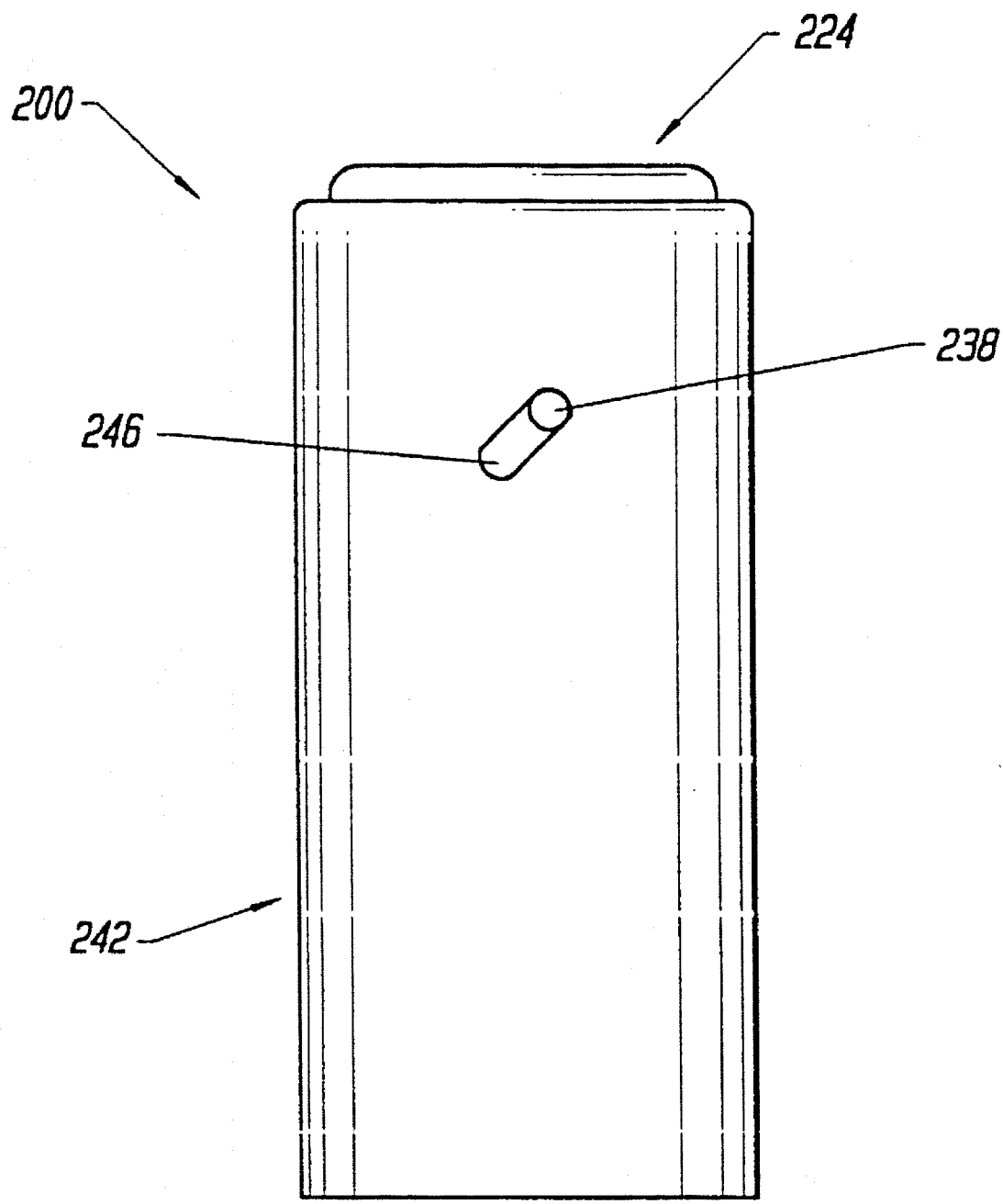
FIG. 9 shows a side view of another embodiment of the assembled lancet device.
Figure 13:
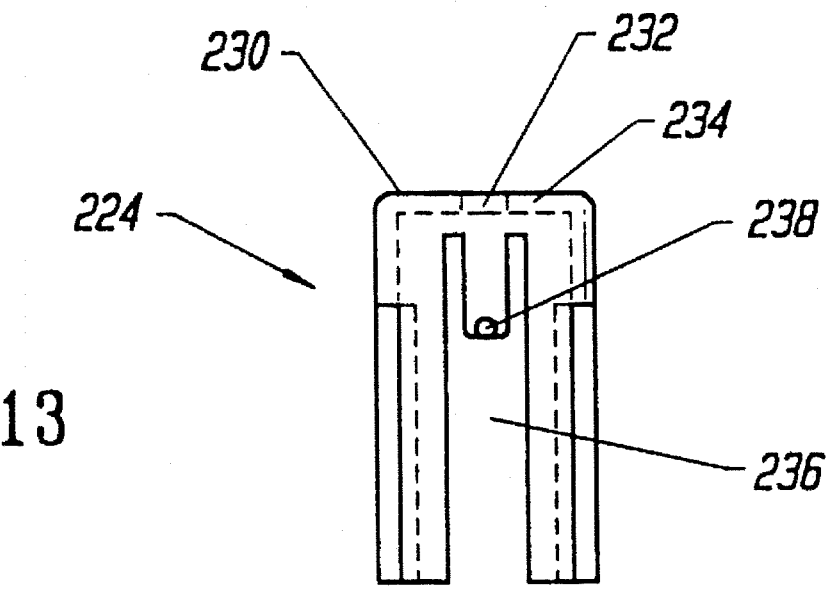
FIG. 13 is a side view of the trigger of the embodiment shown in FIG. 9.
Figure 10:
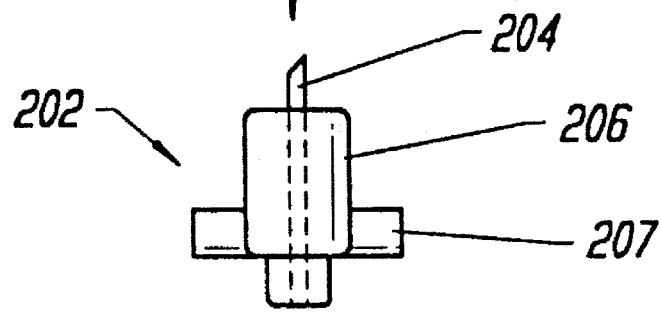
FIG. 10 is a side view of the lance of the embodiment shown in FIG. 9.
Figure 11:
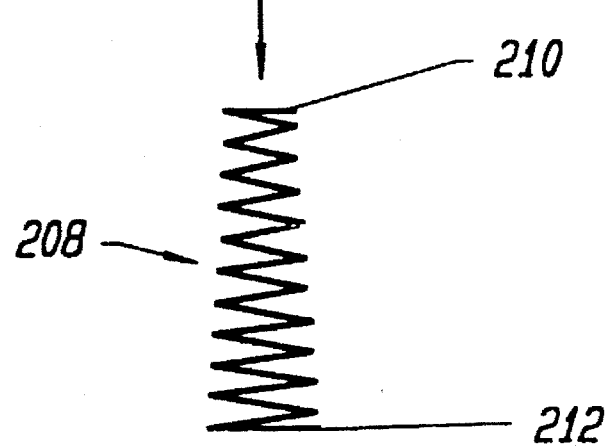
FIG. 11 is a side view of the spring of the embodiment shown in FIG. 9.
Figure 12A:
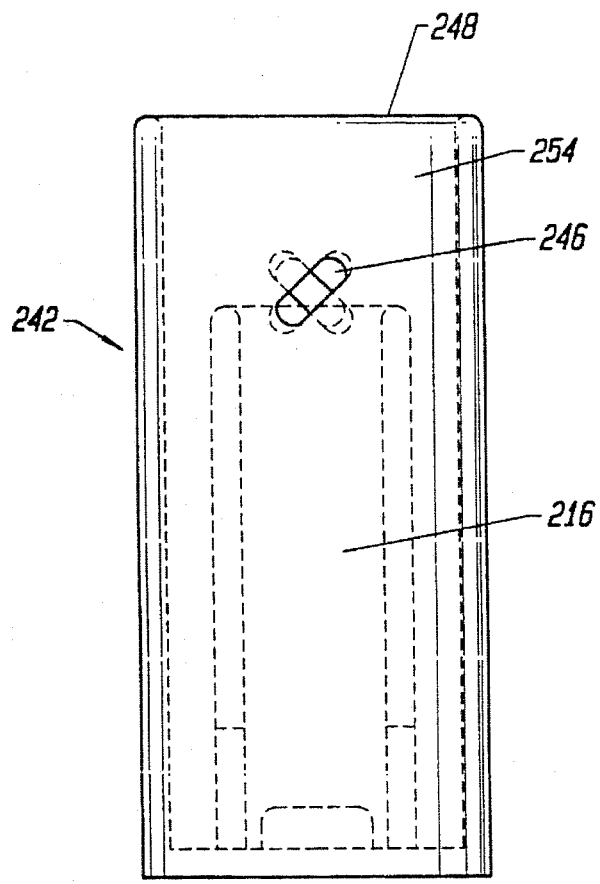
FIGS. 12a and 12b are side views of the body of the embodiment shown in FIG. 9.
Figure 12B:
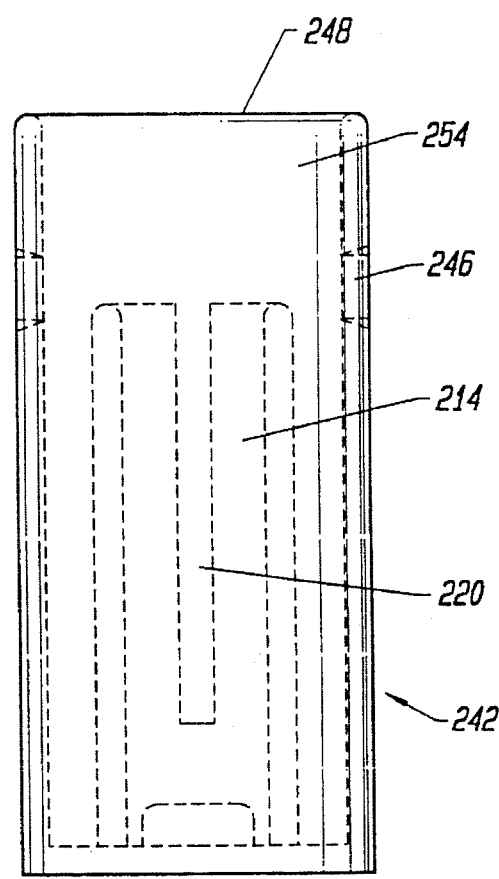
Figure 14:
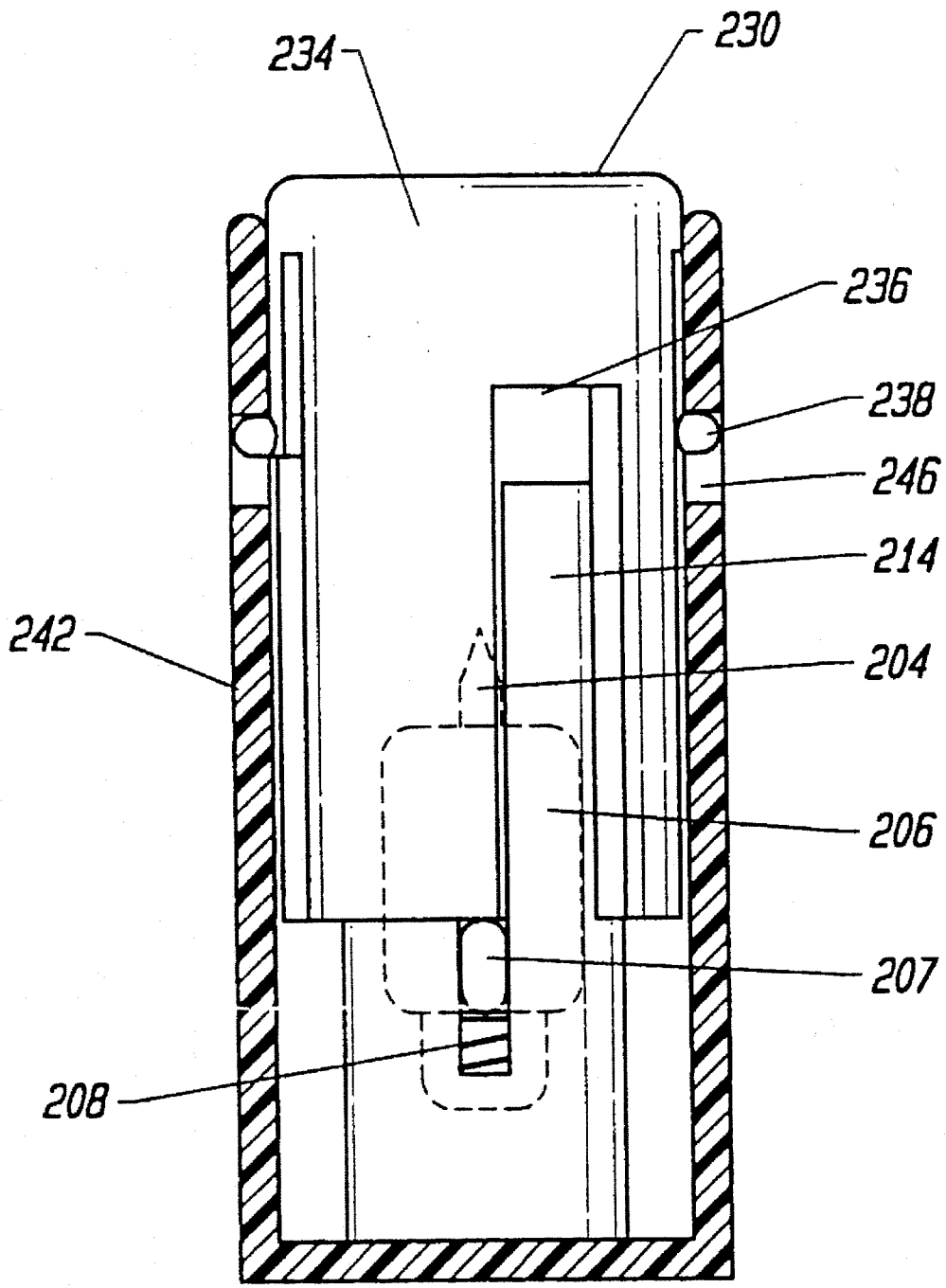
FIG. 14 is a longitudinal cross-section through the assembled lancet device of the embodiment shown in FIG. 9.

In another embodiment the disposable lancet device 200 shown assembled in FIGS. 9 and 14 and in an exploded view in FIGS. 10–13 comprises a body 242. The trigger 224 is slidably located in barrel 254 of body 242. Its end 230 containing an orifice 232 is aligned so that end 230 is in about the same plane 248 as the open end of body 242.

In a preferred embodiment, end 230 of trigger 224 is aligned in plane 248 by means of pins 238 of trigger 224 and slots 246 of body 242.

Means are provided for guiding and centering trigger 224 in barrel 254 of body 242. In a preferred embodiment, pins 238 of trigger 224 and slots 246 of body 242 serve this function as well.

The base 214 is inside barrel 254 of body 242. In a preferred embodiment, base 214 is a portion of the same molded piece as body 242.

Spring 208 is fixedly attached to base 214 at end 212. Spring 208 is fixedly attached to shaft 206 of lance 202 at end 210. Spring 208, shaft 206 and needle 204 thus provide a lance means. In a preferred embodiment, end 212 is greater in diameter than end 210 to form a tapered spring configuration. As described in the previous embodiment, using this tapered spring configuration allows the coils of spring 208 to compress within one another without twisting when they are compressed in an armed position. This provides reproducible, centered, piercing force to the lance. In one preferred embodiment, end 212 is about 250 mils in diameter and end 210 is about 150 mils in diameter.

Base 214 comprises well 216 wherein lance 202 and spring 208 are loaded and retained. In a preferred embodiment, shaft 206 of lance 202 has arms 207 which line up with slots 220 in base 214. When trigger 224 is inserted into barrel 254 of base 242, it pushes against arms 207 of lance 202, sliding the lance into well 216 of base 214. This compresses spring 208. When pins 238 of trigger 224 engage slots 246 of body 242, they snap in place, retaining lance 202 and spring 208 in a compressed, armed position in well 216. The lance means is thus located pre-armed in base 214 during manufacture, shipping and storage of the device prior to use.

To use lancet device 200, a body part, such as a finger, to be pierced is placed over orifice 232 and trigger 224 is then depressed. Pins 238 sliding in angled slots 246 cause trigger 224 to rotate. When trigger 224 is fully depressed slots 236 are aligned with slots 220 of base 214. This releases lance 202 and spring 208. Slots 246 can be at angles from 10° to 80°. In a preferred embodiment, the angle of slots 246 can be from 30° to 60°.

Figure 15:
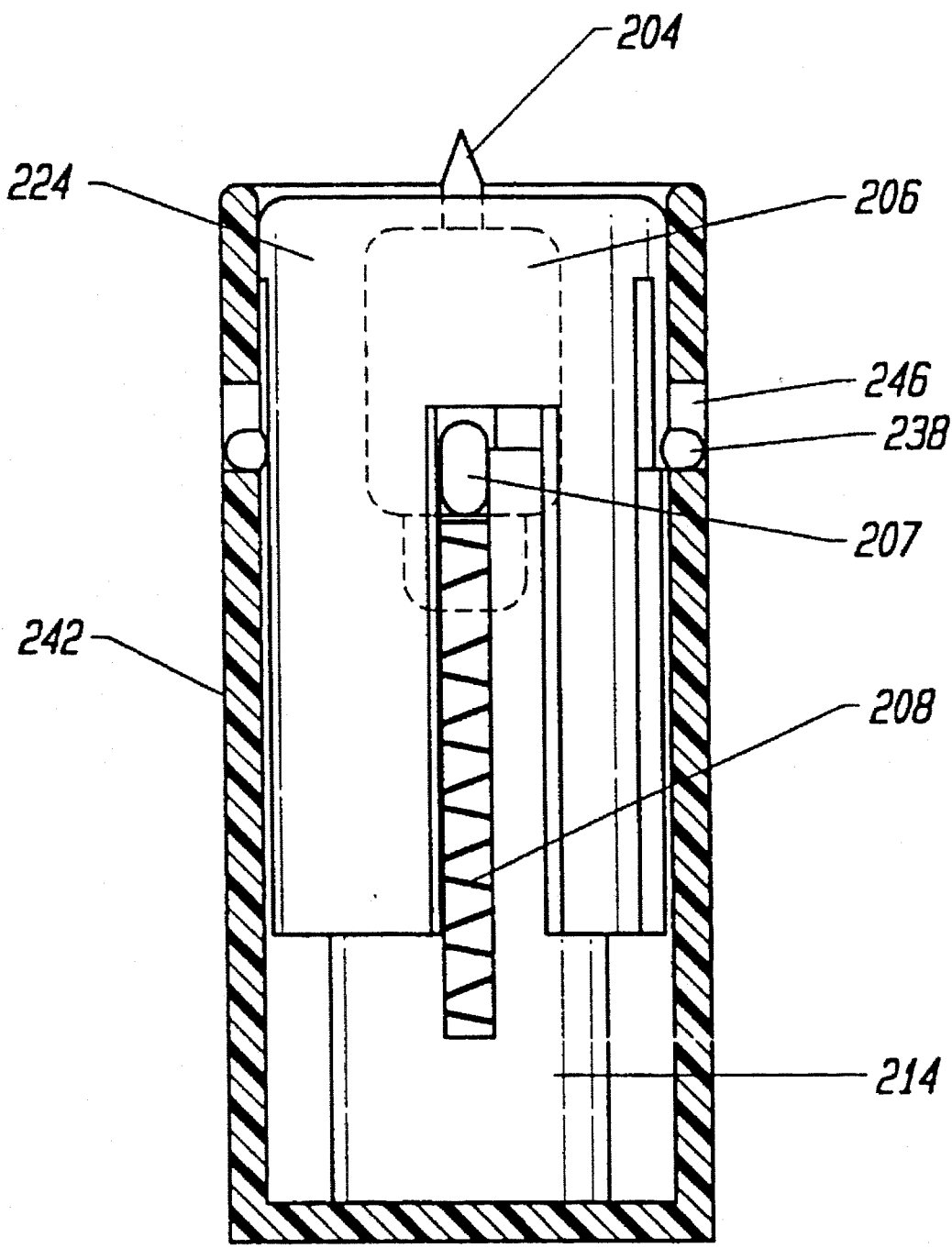
FIG. 15 shows the lancet device of the embodiment shown in FIG. 9 in firing position.

Lance 202 is centered and guided by shaft 206 and arms 207 within base 214. The force of decompression of spring 208 pushes needle 204 through orifice 232 to pierce the finger depressing trigger 224. This can be seen in FIG. 15. The depth of penetration of needle 204 is controlled by the length of the needle and the thickness of end wall 234. Because the body part to be pierced is the body part which depresses trigger 224, this lancet device is self-activating. This feature makes the lancet device of the present invention simple to use, as it may be operated with one hand. In one preferred embodiment, end wall 234 is 20 to 60 mils thick and the protruding portion of needle 204 is 1 to 2.5 mm long.

Figure 8:
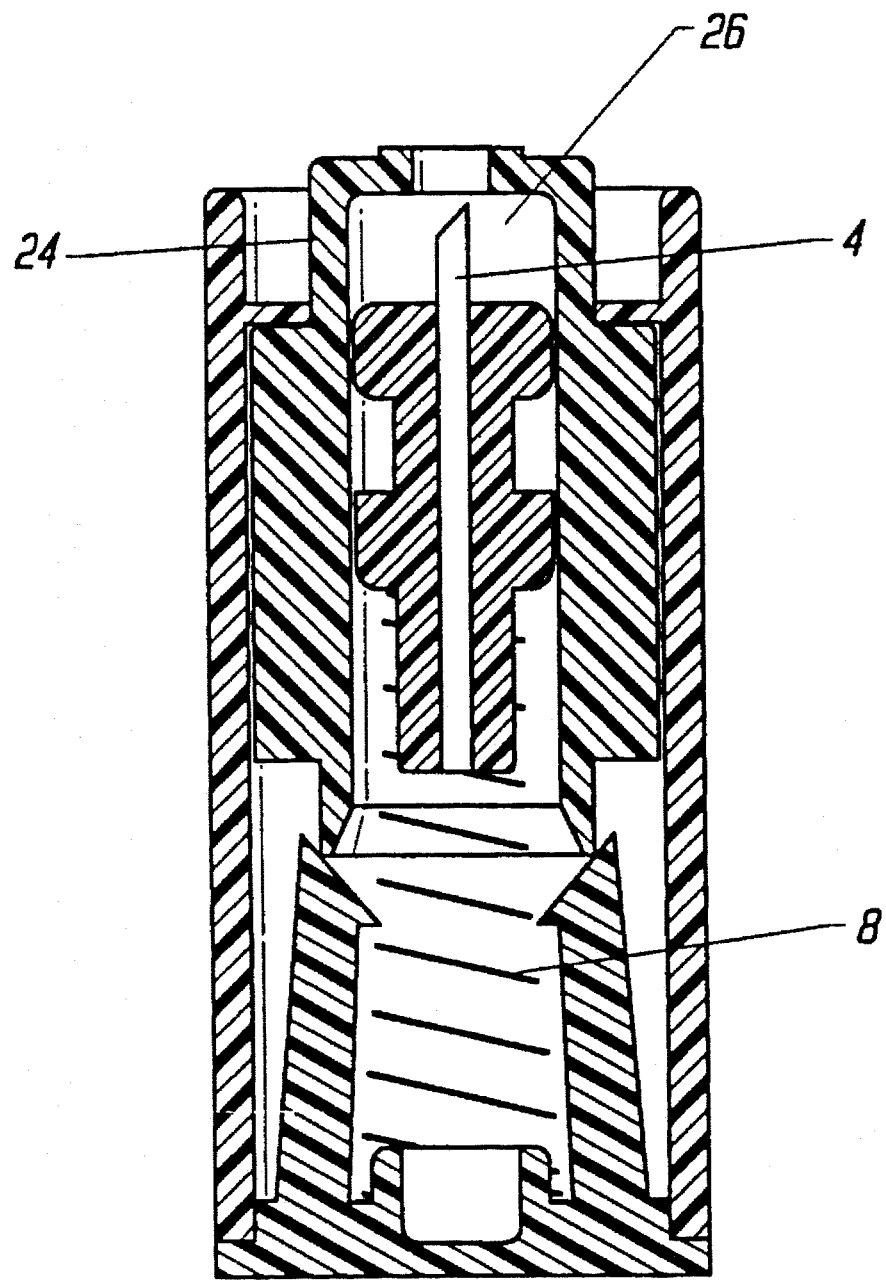
FIG. 8 shows the lancet device of the embodiment shown in FIG. 1 in the retracted position after it has been fired.
Figure 16:
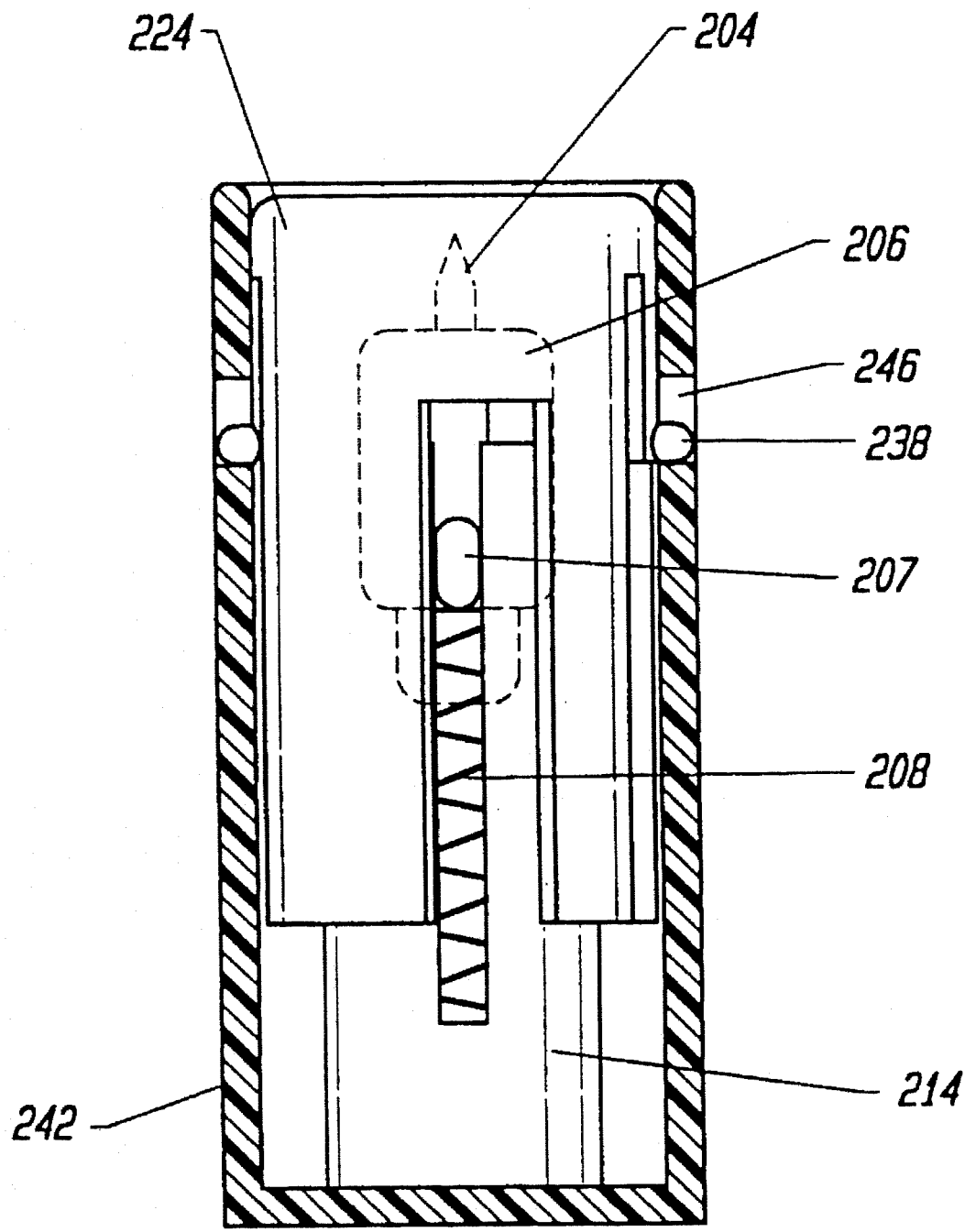
FIG. 16 shows the lancet device of the embodiment shown in FIG. 9 in the retracted position after it has been fired.

In either embodiment, when the spring completes its over-extension after release and returns to its regular, unarmed length, the needle is completely within the trigger, so there is little or no danger of accidental needle exposure from the device after use. This can be seen in FIGS. 8 and 16.

The shaft of the lance is greater in diameter than the orifice in the trigger to prevent over-extension of the needle. The orifice is greater in diameter than the needle to allow easy withdrawal of the needle back into the hollow center of the trigger.

Figure 17A:
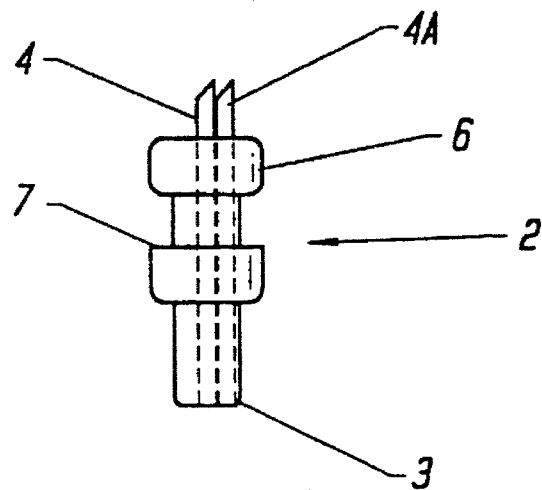
FIGS. 17a and 17b show side views of the alternate lance for each embodiment.
Figure 17B:
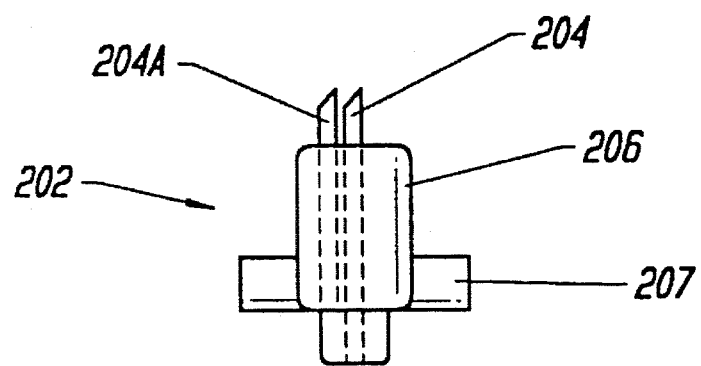

In either embodiment, more than one needle may be included in the lance. This alternate configuration may provide a more suitable incision for some uses. In preferred embodiments, as seen in FIGS. 17a and 17b, two needles are used.

Various dimensions, shapes and structures can be used for the various components of the lancet device of the present invention.

The body, trigger, shaft, edge, and base may be circular, oval, square, rectangular or other appropriate shape in cross-section.

Conveniently, the base, trigger and body are injection molded using an appropriate plastics material. In a preferred embodiment, they are made of polystyrene.

The lancet device of the present invention may be utilized for human or veterinary use.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A lancet device for piercing human or other animal tissue, comprising:

a lance, including a needle of a specific length and a shaft with an edge;

a tapered spring, the narrow diameter end of which is fixedly attached to said shaft of said lance;

a base, including a well wherein said lance and spring are located, and a plurality of arms with clips to hold said edge of said shaft of said lance for retaining said lance and spring in a compressed armed position prior to use;

means for fixedly attaching the large diameter end of said spring to said base;

a trigger, including a barrel with an outer surface and a hollow center to slidably accept said lance, an end with an orifice to allow said needle to protrude through said orifice when said lance and spring are released from said armed position to pierce the human or other animal tissue, said end having a specific wall thickness for controlling the depth of penetration of said needle of specific length into said tissue, and clip-deflecting edges to spread said arms and release said lance and spring from said armed position when said trigger is depressed by a body part to be pierced;

a body, including a barrel with an inner surface, a hollow center, apertures in both ends to slidably accept said trigger and fixedly accept said base, a ring on the inner surface of the body, and a lip extending out from a first end of said body, a distal end of said lip being in about the same plane as the face of said orifice-containing end of said trigger when said trigger is inserted into said body;

means for fixedly attaching said base to said body; and a ring on said outer surface of said trigger, wherein, when the device is in the armed position, the trigger ring abuts the body ring to align said orifice-containing end of said trigger in a plane with said body lip.

2. A device as in claim 1 wherein said lance includes a plurality of needles.

3. A device as in claim 1 wherein said base, trigger and body are made of polystyrene.

4. A device as in claim 1 wherein said base, trigger and body are injection molded.

5. The lancet device of claim 1, wherein the device can be constructed by:

(a) inserting the trigger into the body through the base-accepting aperture until the trigger contacts the body ring; and (b) inserting the base, spring and lance, wherein the lance is retained by the clips, into the base-accepting aperture until the base if fixedly accepted by the body.

* * * * *